US012575733B2

(12) United States Patent
Nishida

(10) Patent No.: US 12,575,733 B2
(45) Date of Patent: Mar. 17, 2026

(54) STORAGE MEDIUM, IMAGE MANAGEMENT APPARATUS, READING TERMINAL, AND IMAGE MANAGEMENT SYSTEM

(71) Applicant: Konica Minolta, Inc., Tokyo (JP)

(72) Inventor: Yasuhiko Nishida, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 533 days.

(21) Appl. No.: 17/900,150

(22) Filed: Aug. 31, 2022

(65) Prior Publication Data

US 2023/0069155 A1 Mar. 2, 2023

(30) Foreign Application Priority Data

Sep. 1, 2021 (JP) ................................. 2021-142494

(51) Int. Cl.

| | |
|---|---|
| *A61B 5/00* | (2006.01) |
| *A61B 6/00* | (2006.01) |
| *G01R 33/54* | (2006.01) |
| *G06T 7/00* | (2017.01) |

(52) U.S. Cl.
CPC .......... *A61B 5/0033* (2013.01); *A61B 6/5223* (2013.01); *G01R 33/543* (2013.01); *G06T 7/0012* (2013.01)

(58) Field of Classification Search
CPC ..... A61B 5/0033; A61B 6/5223; A61B 6/032; A61B 6/465; A61B 6/488; A61B 6/5229; A61B 5/0037; A61B 5/743; A61B 5/748; A61B 2576/00; G01R 33/543; G01R 33/5608; G06T 7/0012
See application file for complete search history.

(56) References Cited

U.S. PATENT DOCUMENTS

| | | | | |
|---|---|---|---|---|
| 2009/0087049 A1* | 4/2009 | Takahashi | .............. | G16H 15/00 |
| | | | | 382/128 |
| 2012/0183191 A1* | 7/2012 | Nakamura | ............. | G16H 30/40 |
| | | | | 382/128 |
| 2012/0250961 A1* | 10/2012 | Iwasaki | .................. | G16H 15/00 |
| | | | | 382/128 |
| 2017/0303868 A1* | 10/2017 | Lee | ....................... | G06T 11/006 |
| 2023/0069155 A1* | 3/2023 | Nishida | ................ | G01R 33/543 |

FOREIGN PATENT DOCUMENTS

| | | |
|---|---|---|
| JP | H08166995 A | 6/1996 |
| JP | 2016-187568 A | 11/2016 |
| JP | 2017-072936 A | 4/2017 |
| JP | 2019-202087 A | 11/2019 |

OTHER PUBLICATIONS

Office Action issued in counterpart Japanese Patent Application No. 2021-142494 mailed Oct. 7, 2025 (7 pages).
Office Action issued in Japanese Application No. 2021-142494; Dated Jun. 25, 2025 (10 pages).

* cited by examiner

*Primary Examiner* — Md K Talukder
(74) *Attorney, Agent, or Firm* — Osha Bergman Watanabe & Burton LLP

(57) ABSTRACT

A non-transitory computer readable storage medium stores instructions causing a computer that processes information stored in an image management apparatus to execute: creating a synthesized image by synthesizing a scout image in a predetermined region of a slice image, the slice image and the scout image being stored in the image management apparatus, and the scout image specifying a cross-section position of the slice image.

8 Claims, 11 Drawing Sheets

1

STORAGE MEDIUM, IMAGE MANAGEMENT APPARATUS, READING TERMINAL, AND IMAGE MANAGEMENT SYSTEM

CROSS-REFERENCE TO RELATED APPLICATIONS

The entire disclosure of Japanese Patent Application No. 2021-142494, filed on Sep. 1, 2021, is incorporated herein by reference.

BACKGROUND

Technical Field

The present invention relates to a storage medium, an image management apparatus, a reading terminal, and an image management system.

Description of Related Art

In recent years, computerization of information has also progressed in a medical field, and a medical image generated through an imaging test on a patient is managed as electronic data. For example, a slice image (cross-section image) captured through computed tomography (CT), magnetic resonance imaging (MRI), or the like, and a scout image that is a positioning image for determining a imaging range are known. There is a case where the scout image is utilized for specifying a cross-section position of the slice image.

In related art, in a medical image viewer, a slice image and a scout image in the same examination can be displayed side by side, and by displaying a mark indicating a cross-section position of the slice image on the scout image, it is possible to indicate the position of the slice image in a body of a patient (see JP 2017-72936A).

However, in a case where a slice image and a scout image are attached to a reading report and stored, the slice image and the scout image are respectively selected and attached to the reading report. Further, also in a case where a slice image and a scout image are stored in an external apparatus such as an electronic health record, the slice image and the scout image are respectively selected.

Thus, in a case where a slice image and a scout image are attached on a reading report side by side, or in a case where a slice image and a scout image are displayed on an electronic health record side by side, it is not necessarily guaranteed that images having a correspondence relationship are attached or displayed side by side. For example, a slice image and a scout image not having a correspondence relationship can be respectively selected and can be attached on the reading report. In other words, while a slice image and a scout image are associated with each other in an image management apparatus that manages medical images, a correspondence relationship between the slice image and the scout image is unclear in a state where the slice image and the scout image are attached on the reading report or the electronic health record.

SUMMARY

One or more embodiments of the present invention provide a practical and technological improvement over conventional storage mediums, image management apparatuses, reading terminals, and image management systems. For example, one or more embodiments enable recognition of a correspondence relationship between a slice image and a scout image outside an image management apparatus.

According to an aspect of the present invention, there is provided a non-transitory computer readable storage medium storing instructions causing a computer that processes information stored in an image management apparatus that stores a slice image and a scout image for specifying a cross-section position of the slice image, to execute creating a synthesized image by synthesizing the scout image in a predetermined region of the slice image.

According to another aspect of the present invention, there is provided an image management apparatus that stores a slice image and a scout image for specifying a cross-section position of the slice image, the image management apparatus including a hardware processor that creates a synthesized image by synthesizing the scout image in a predetermined region of the slice image.

According to another aspect of the present invention, there is provided a reading terminal that processes information stored in an image management apparatus that stores a slice image and a scout image for specifying a cross-section position of the slice image, the reading terminal including a hardware processor that creates a synthesized image by synthesizing the scout image in a predetermined region of the slice image.

According to another aspect of the present invention, there is provided an image management system including an image management apparatus that stores a slice image and a scout image for specifying a cross-section position of the slice image, the image management system including a hardware processor that creates a synthesized image by synthesizing the scout image in a predetermined region of the slice image.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein.

DETAILED DESCRIPTION OF THE EMBODIMENTS

Hereinafter, embodiments of an analysis device, an analysis method, and a recording medium will be described. However, the scope of the invention is not limited to the illustrated examples.

Embodiments of a non-transitory computer readable storage medium storing instructions, an image management apparatus, a reading terminal, and an image management system will be described below. However, a scope of the invention is not limited to the illustrated examples.

First Embodiment

First, a first embodiment of the present invention will be described.

Figure 1:
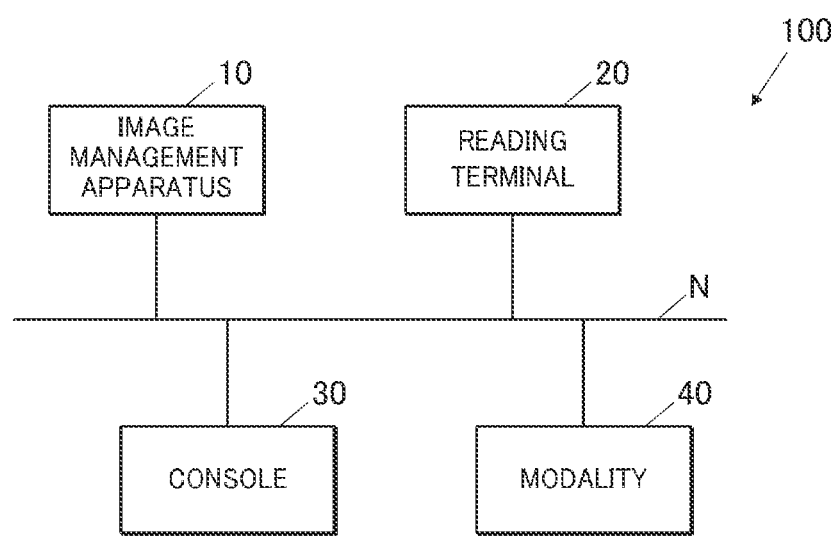
FIG. 1 is a system configuration diagram of an image management system in a first embodiment of the present invention.

FIG. 1 illustrates a system configuration of an image management system 100.

As illustrated in FIG. 1, the image management system 100 includes an image management apparatus 10, a reading terminal 20, a console 30, a modality 40, and the like, and is connected so as to be able to perform data communication via a communication network N such as a local area network (LAN). The respective apparatuses that constitute the image management system 100 conform to health level seven (HL7) and digital image and communications in medicine (DICOM) standards, and communication among the respective apparatuses is performed in conformity to HL7 and DICOM. Further, the communication may be performed in conformity to predetermined communication standards defined among the respective apparatuses. Note that the number of reading terminals 20 and the number of modalities 40 are not particularly limited.

The image management apparatus 10 stores and manages image data of a medical image generated at the modality 40. Examples of the image management apparatus 10 can include a picture archiving and communication system (PACS), and the like. The PACS includes a reading report management apparatus that manages the reading report.

The reading terminal 20 is a computer apparatus such as a personal computer (PC) to be used by a reading doctor. The reading doctor performs reading of a medical image, creation of a reading report, and the like, at the reading terminal 20.

The console 30 outputs imaging conditions to the modality 40 and controls imaging operation by the modality 40.

The modality 40, which is an imaging apparatus such as CT, MRI, a radiographic imaging apparatus (DR, CR) and an ultrasonic diagnostic apparatus (US), images a patient to generate a medical image. The modality 40 attaches supplementary information to the medical image by writing the supplementary information in a header of an image file of the medical image in conformity to the DICOM standards.

The modality 40 images a target portion of a target patient in accordance with operation by a medical technologist at the console 30 and transmits the generated medical image to the image management apparatus 10.

Figure 2:
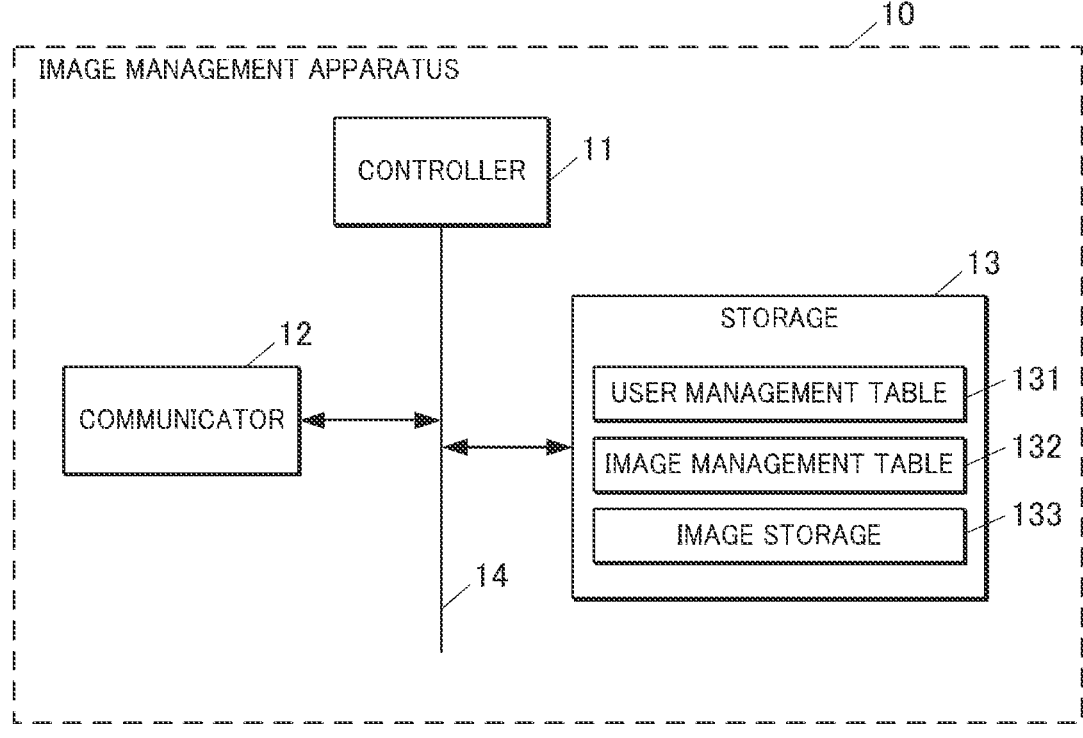
FIG. 2 is a block diagram illustrating a functional configuration of an image management apparatus.

FIG. 2 illustrates a functional configuration of the image management apparatus 10.

As illustrated in FIG. 2, the image management apparatus 10 includes a controller 11, a communicator 12, a storage 13, and the like, which are connected by a bus 14.

The controller 11 includes a central processing unit (CPU), a random access memory (RAM), and the like, and comprehensively controls processing operation of the respective units of the image management apparatus 10. Specifically, the CPU reads various kinds of instructions (e.g., processing programs) stored in the storage 13, loads the instructions to the RAM and performs various kinds of processing in cooperation with the instructions.

The communicator 12, which is constituted with a network interface, and the like, transmits/receives data to/from an external apparatus connected via the communication network N. For example, the communicator 12 receives the medical image obtained by imaging the patient with the modality 40.

The storage 13, which is constituted with a hard disk drive (HDD), a solid state drive (SSD), and the like, stores various kinds of data. For example, a user management table 131 and an image management table 132 are stored in the storage 13. Further, the storage 13 includes an image storage 133 that stores image data of a medical image.

The user management table 131 is a table for managing users (health personnel) who utilize an image management service provided by the image management apparatus 10. In the user management table 131, a user ID, a password, name, affiliation, and the like, are stored in association with each other for each user.

The image management table 132 is a table for managing medical images stored in the image storage 133. In the image management table 132, supplementary information of medical images is stored in association with the medical images for each medical image. The supplementary information includes patient information, examination information, series information and image information.

The patient information is information regarding a patient. The patient information includes a patient ID, patient name, birth date, age, gender, and the like.

The examination information is information regarding an examination. The examination information includes an examination instance UID, examination date and time, examination description, and the like.

The series information is information regarding a series. The series information includes a modality (such as CT, MRI, DR, CR and US), a series instance UID, an examination portion, a series number, series description, and the like. The series instance UID is a unique ID for identifying a series. The series number is a number indicating order of series in the same examination and is sometimes utilized as a display order, or the like.

The image information is information regarding a medical image. The image information includes an SOP instance UID, an image number, image generation date and time, an imaging direction, an imaging start position, a slice thickness, an image type, a file path, and the like. The image number is a number indicating the ordinal number of the image within the same series. The imaging start position is a coordinate indicating a position at which an examination (scanning) is started (particularly, a position in a direction orthogonal to an image plane of each slice image) in the examination such as CT and MRI. The slice thickness is a thickness of a slice image (cross-section image, tomographic image) in a direction orthogonal to an image plane of each slice image in the examination such as CT and MRI. The image type is information indicating whether the image is a slice image or a scout image in the examination such as CT and MRI. The file path is information indicating a storage location of the medical image.

In the image storage 133, for example, a slice image and a scout image for specifying a cross-section position of the slice image, captured in the examination such as CT and MRI, are stored.

The slice image is each of a plurality of cross-section images (tomographic images) generated at predetermined intervals (slice thickness) along a predetermined direction (for example, a body axis direction).

The scout image, which is an image viewed from a viewpoint different from a viewpoint of the slice image, is constituted with a plane orthogonal to an image plane of the slice image. The scout image is a positioning image for determining an imaging range.

Further, in the storage 13, a reading report created in response to an operation instruction from the reading terminal 20 is stored.

In a case where there is an acquisition request of a medical image from an external apparatus, the controller 11 transmits display data for displaying the requested medical image to the external apparatus via the communicator 12 in response to the acquisition request.

Figure 3:
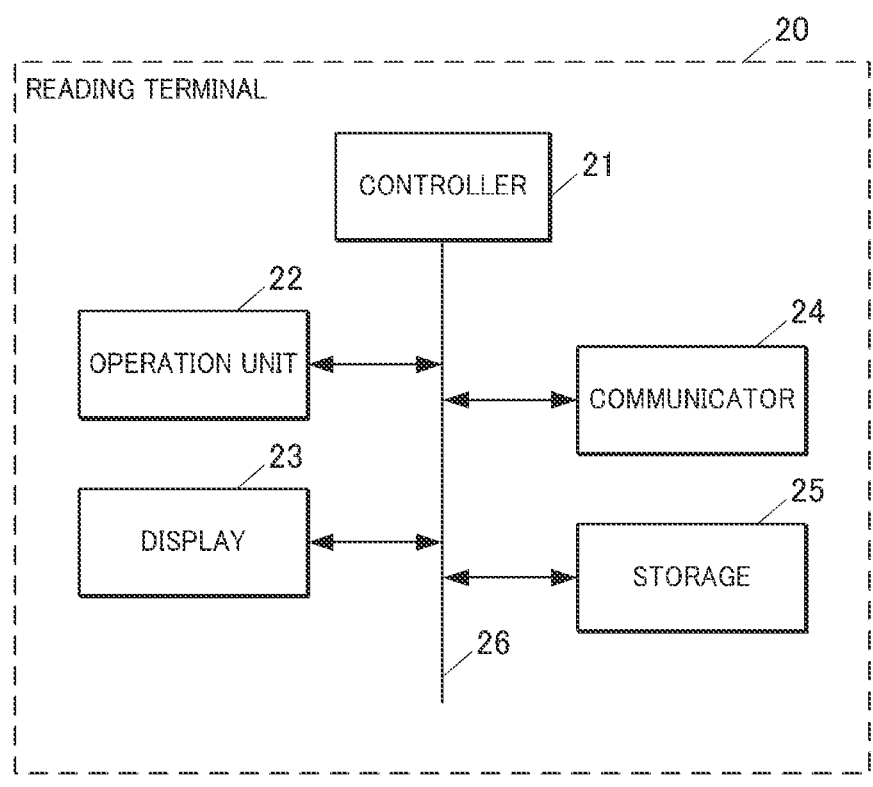
FIG. 3 is a block diagram illustrating a functional configuration of a reading terminal.

FIG. 3 illustrates a functional configuration of the reading terminal 20.

As illustrated in FIG. 3, the reading terminal 20 includes a controller 21, an operation unit 22, a display 23, a communicator 24, a storage 25, and the like, which are connected by a bus 26.

The controller 21, which is constituted with a CPU, a RAM, and the like, comprehensively controls processing operation of the respective units of the reading terminal 20. Specifically, the CPU reads various kinds of the instructions stored in the storage 25, loads the instructions to the RAM and performs various kinds of processing in cooperation with the instructions.

The operation unit 22, which includes a keyboard including a cursor key, character/number input keys, various kinds of function keys, and the like, and a pointing device such as a mouse, outputs an operation signal input through key operation on the keyboard and mouse operation, to the controller 21.

The display 23, which includes a monitor such as a liquid crystal display (LCD), displays various kinds of screens in accordance with an instruction of a display signal input from the controller 21.

The communicator 24, which is constituted with a network interface, and the like, transmits/receives data to/from an external apparatus connected via the communication network N.

The storage 25, which is constituted with an HDD, an SSD, and the like, stores various kinds of data.

The controller 21 processes information stored in the image management apparatus 10 that stores a slice image and a scout image for specifying a cross-section position of the slice image.

The controller 21 (creation means, a hardware processor) creates a synthesized image by synthesizing the scout image in a predetermined region of the slice image.

Here, the controller 21 creates the synthesized image in a state where a reference line indicating the cross-section position of the slice image is added on the scout image.

The controller 21 creates a synthesized image by synthesizing the scout image in a predetermined region of the slice image in a case where a second user operation is performed in addition to a first user operation or in response to a second user operation performed in addition to a first user operation.

Specifically, an operation of dragging and dropping the scout image with respect to the slice image is used as the "first user operation", and pressing a predetermined key (such as a Ctrl key and an Alt key) is used as the "second user operation". Note that the "first user operation" and the "second user operation" are not limited to these examples.

The controller 21 outputs the created synthesized image. Specifically, the controller 21 causes the synthesized image to be displayed at the display 23. The controller 21 may transmit the synthesized image to an external apparatus via the communicator 24.

Operation in the image management system 100 will be described next.

Figure 4:
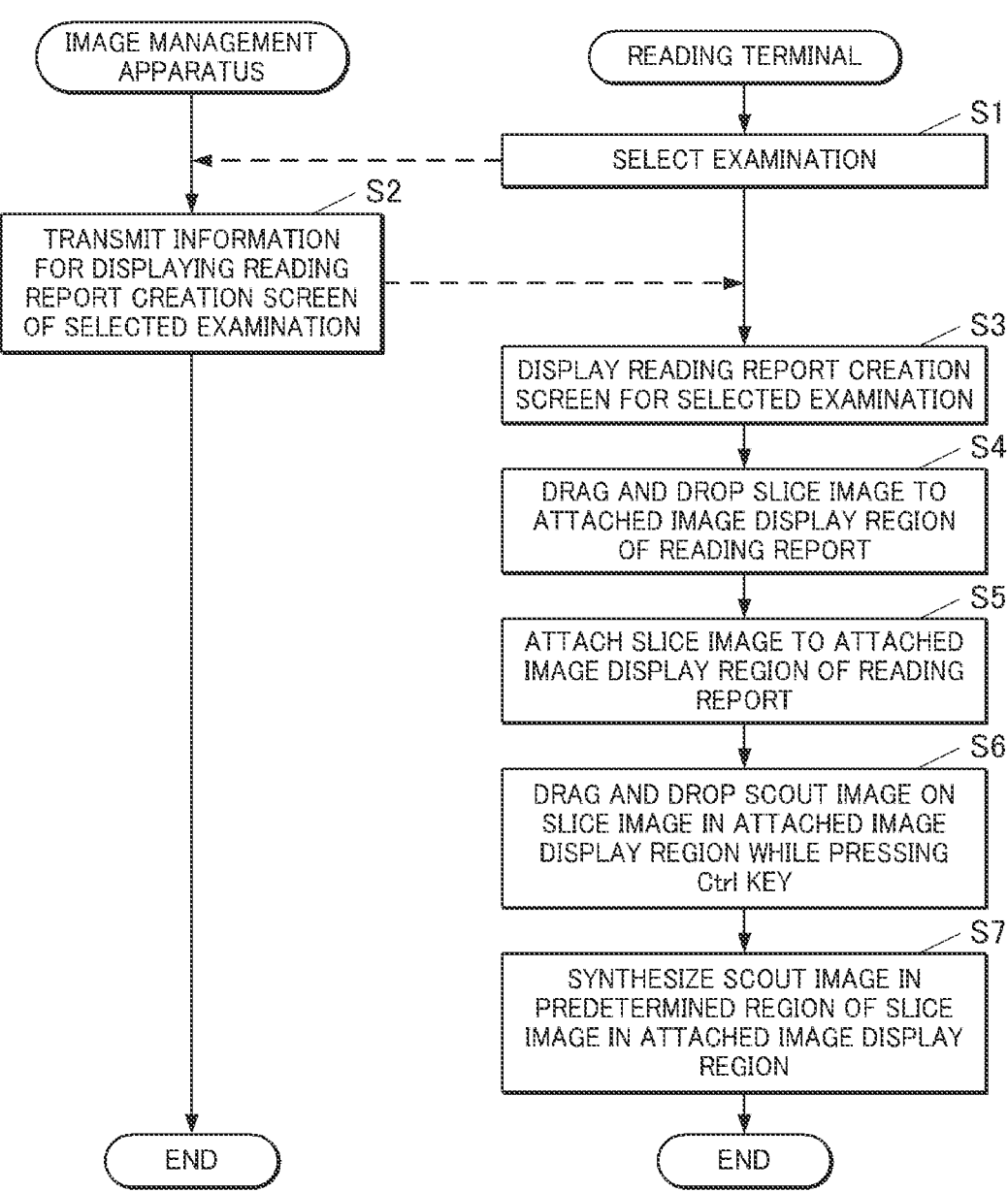
FIG. 4 is a ladder chart indicating first reading report creation processing in the first embodiment.

FIG. 4 is a ladder chart indicating first reading report creation processing to be executed at the image management apparatus 10 and the reading terminal 20.

First, if the image management apparatus 10 is accessed from the reading terminal 20 in accordance with operation by the user (reading doctor), the controller 11 of the image management apparatus 10 performs log-in processing. Specifically, the controller 11 determines that the user is a legitimate user in a case where a user ID and a password input at the operation unit 22 of the reading terminal 20 matches one of combinations of user IDs and passwords registered in advance in the user management table 131.

After the log-in processing, if the user selects an examination for which reading is to be performed through operation from the operation unit 22 of the reading terminal 20 (step S1), the controller 11 of the image management apparatus 10 transmits information (for example, information regarding a medical image) for displaying a reading report creation screen of the selected examination to the reading terminal 20 via the communicator 12 (step S2). It is assumed here that the selected examination is an examination such as CT and MRI in which medical images including a slice image are generated.

The controller 21 of the reading terminal 20 acquires information for displaying the reading report creation screen of the selected examination from the image management apparatus 10 via the communicator 24 and causes the reading report creation screen of the selected examination to be displayed at the display 23 (step S3).

Figure 5:
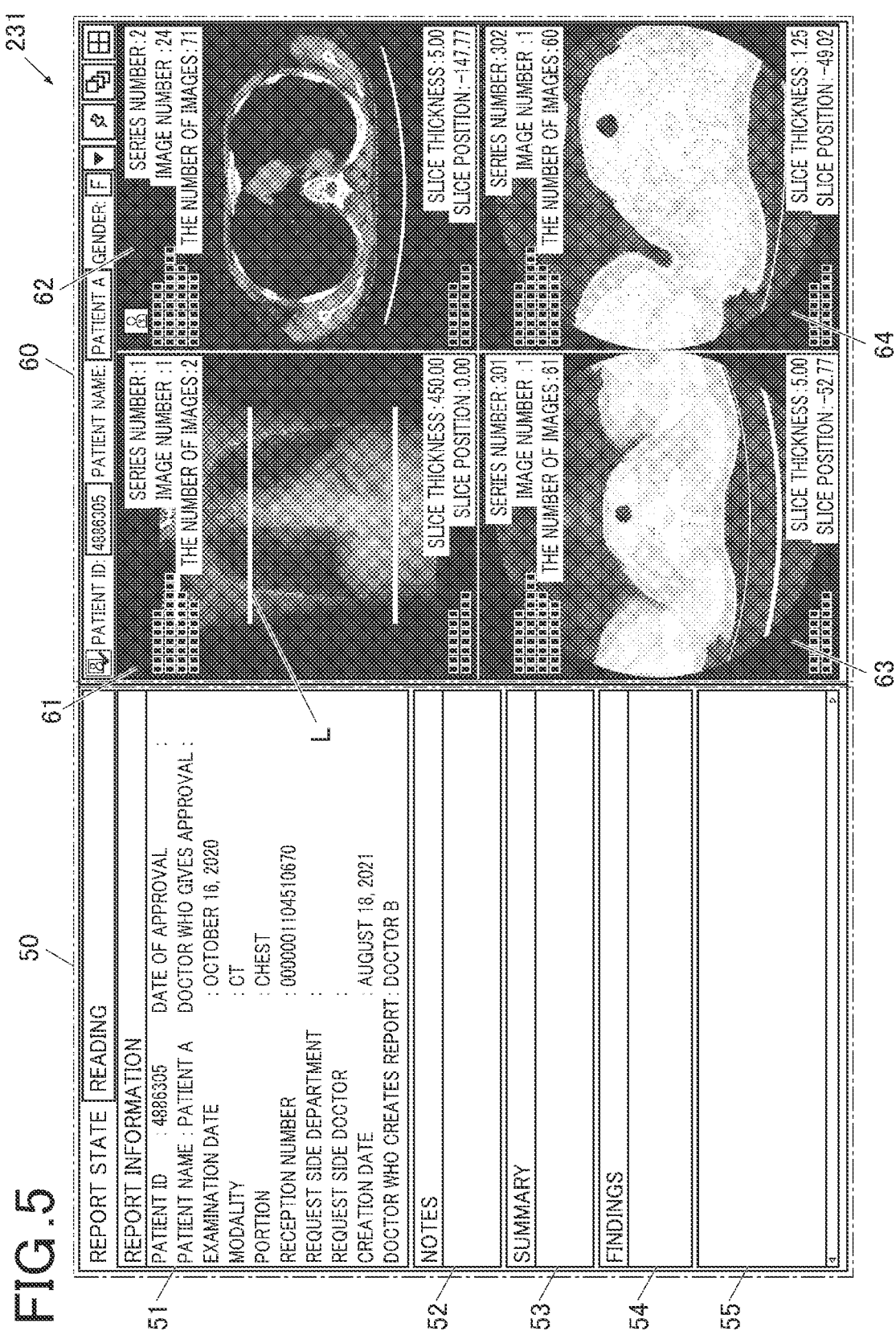
FIG. 5 is an example of a reading report creation screen to be displayed on the reading terminal.

FIG. 5 illustrates an example of the reading report creation screen 231 to be displayed at the display 23 of the reading terminal 20. The reading report creation screen 231 includes a report input screen 50 and a reading screen 60.

The report input screen 50 is a screen for inputting a reading report for the selected examination. The report input screen 50 includes a report information display region 51, a note input region 52, a summary input region 53, a finding input region 54, and an attached image display region 55.

In the report information display region 51, information regarding the reading report such as a patient ID, patient name, examination date, a modality and a portion relating to the selected examination is displayed.

The note input region 52, the summary input region 53 and the finding input region 54 are respectively regions to be used by the user to input notes, summary and findings as content of the reading report.

In the attached image display region 55, a thumbnail image of the medical image selected by the user to be attached to the reading report is displayed. "Attaching the medical image to the reading report" refers to disposing the medical image in a predetermined region (here, the attached image display region 55) of the reading report to display the medical image. When the stored reading report is viewed later, the medical image is displayed in the predetermined region of the reading report.

The reading screen 60 is a screen for displaying the medical image to allow the doctor to read the medical image. In the reading screen 60, the medical image captured in the selected examination is displayed. The reading screen 60 includes image display regions 61 to 64.

The controller 11 of the image management apparatus 10 extracts a record including an "examination instance UID" corresponding to the selected examination from the image management table 132 and acquires the medical image relating to the selected examination from the image storage 133 on the basis of a "file path" included in the extracted record. Then, the controller 11 transmits each medical image to the reading terminal 20 via the communicator 12 along with supplementary information such as a "series number" and an "image type" included in the extracted record.

The controller 21 of the reading terminal 20 causes each medical image acquired from the image management apparatus 10 to be displayed in the image display regions 61 to 64 for each series on the basis of the "series number" of each medical image.

Further, the controller 21 acquires whether the medical image is a slice image or a scout image from the "image type" of each medical image acquired from the image management apparatus 10.

In FIG. 5, a slice image is displayed in the image display region 62. As the slice image, a representative image in the same series is initially displayed. As the representative image, for example, the first image from the imaging start position, an image around the center in the imaging range, or the like, is used. In the image display region 61, a scout image is displayed, and a reference line L is displayed at a position corresponding to a cross-section position of the slice image displayed in the image display region 62.

The controller 21 of the reading terminal 20 acquires an imaging start position, a slice thickness and an image number of the slice image displayed in the image display region 62 from the image management table 132 stored in the storage 13 of the image management apparatus 10 and calculates a cross-section position of the slice image. Specifically, the controller 21 calculates a distance from the imaging start position in a direction orthogonal to an image plane of the slice image on the basis of the slice thickness and the image number and calculates the cross-section position of the slice image on the basis of the distance and the imaging start position. The controller 21 then adds a reference line L at a position corresponding to the cross-section position of the slice image with respect to the scout image displayed in the image display region 61.

If the user moves the reference line L in a vertical direction on the scout image in the image display region 61 through operation from the operation unit 22 of the reading terminal 20, a display target of the image display region 62 is switched to a slice image at a cross-section position that is the closest to a position of the reference line L after movement.

If the user drags and drops the slice image in the attached image display region 55 of the reading report on the reading report creation screen 231 displayed at the display 23 of the reading terminal 20 through operation from the operation unit 22 (step S4), the controller 21 of the reading terminal 20 attaches the slice image to the attached image display region 55 of the reading report (step S5).

Figure 6:
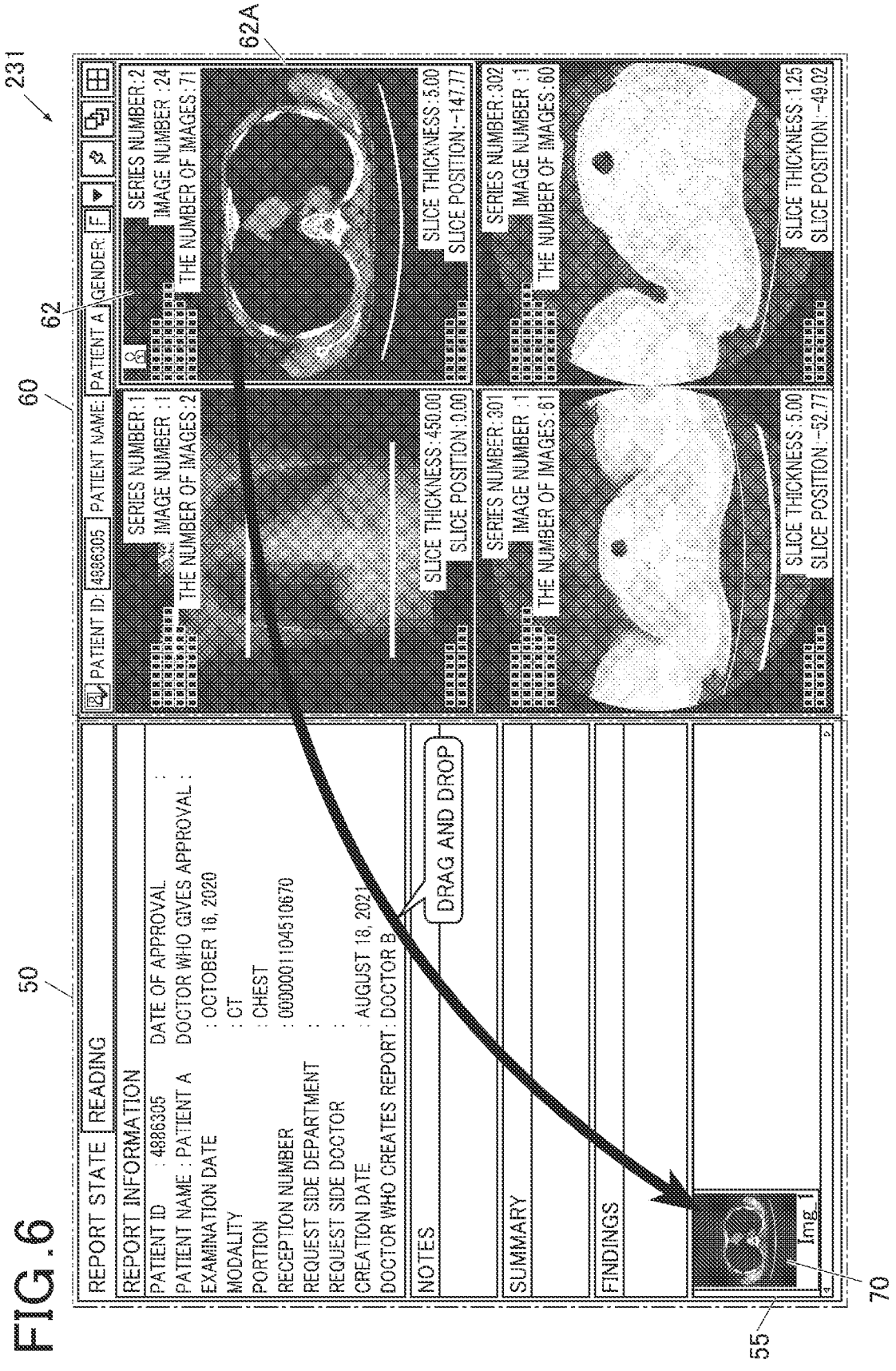
FIG. 6 is a view for explaining operation when a slice image is attached to the reading report on the reading report creation screen.

Specifically, if the user presses a left button of the mouse on the slice image displayed in the image display region 62 on the reading report creation screen 231 illustrated in FIG. 6 through operation from the operation unit 22, an operation target frame 62A is displayed around the slice image. Then, if the user moves the mouse pointer from the slice image to the attached image display region 55 while keeping the left button of the mouse pressed and then releases the finger from the left button of the mouse through operation of the operation unit 22 (drags and drops), a slice image 70 is displayed in the attached image display region 55 of the reading report. The slice image 70 is a thumbnail image of the slice image displayed in the image display region 62.

Then, if the user drags and drops the scout image on the slice image 70 in the attached image display region 55 of the reading report while pressing the Ctrl key through operation from the operation unit 22 on the reading report creation screen 231 displayed at the display 23 of the reading terminal 20 (step S6), the controller 21 of the reading terminal 20 synthesizes the scout image in a predetermined region of the slice image 70 in the attached image display region 55 of the reading report (step S7). In other words, the controller 21 creates a synthesized image by synthesizing the scout image in the predetermined region of the slice image 70. Here, the controller 21 creates the synthesized image in a state where a reference line indicating the cross-section position of the slice image 70 is added on the scout image.

Figure 7:
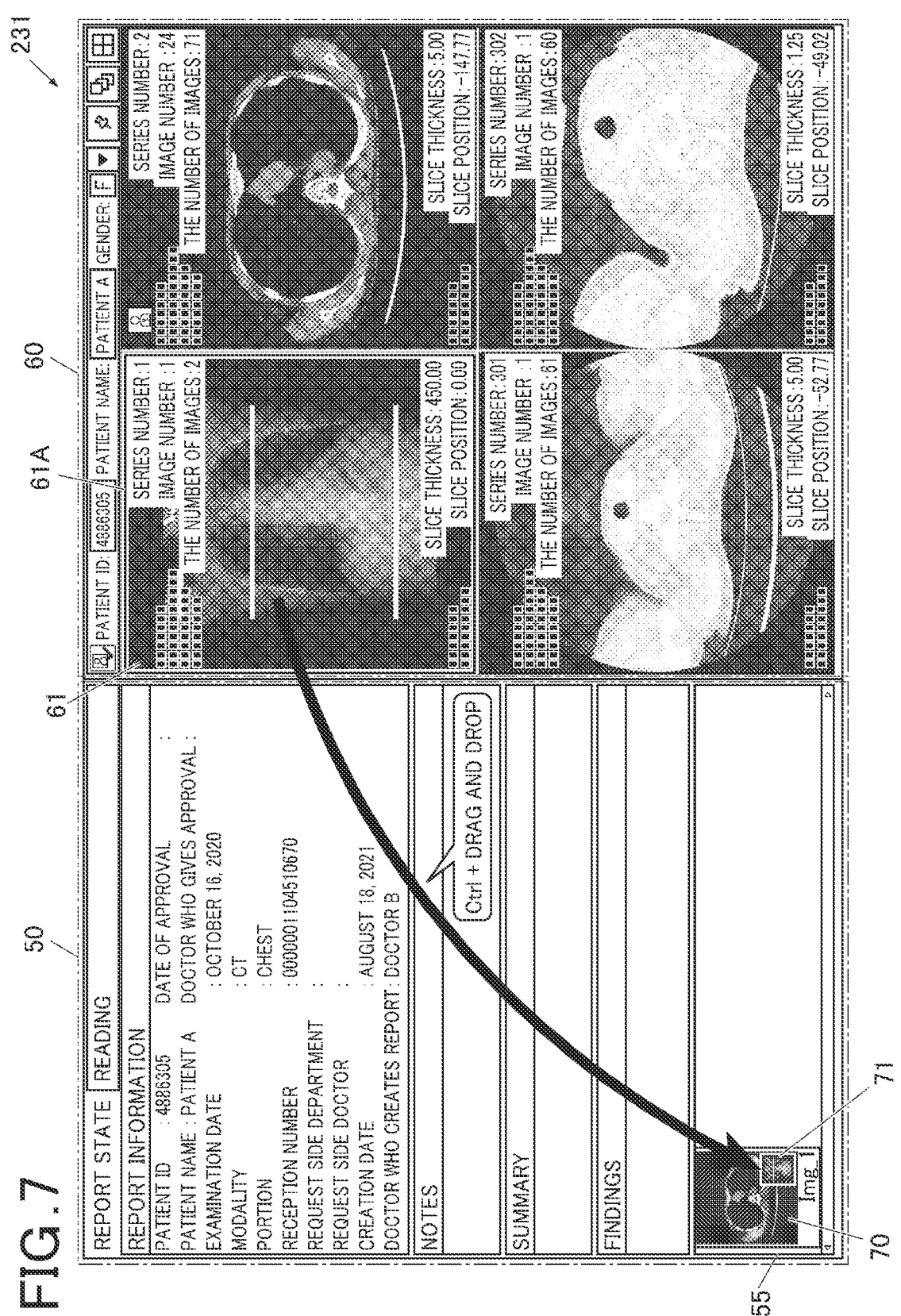
FIG. 7 is a view for explaining operation when a scout image is synthesized on the slice image on the reading report on the reading report creation screen.

Specifically, if the user presses the left button of the mouse on the scout image displayed in the image display region 61 while pressing the Ctrl key through operation from the operation unit 22 on the reading report creation screen 231 illustrated in FIG. 7, an operation target frame 61A is displayed around the scout image. Then, if the user moves the mouse pointer from the scout image to the slice image 70 in the attached image display region 55 through operation from the operation unit 22 while keeping the left button of the mouse pressed and then releases the finger from the left button of the mouse (drags and drops), a scout image 71 is synthesized in a lower right region of the slice image 70 displayed in the attached image display region 55 of the reading report. Note that the user releases the finger that has pressed the Ctrl key after dragging and dropping the scout image. On the scout image 71, which is a scout image displayed in the image display region 61, a reference line indicating the cross-section position of the slice image 70 is added.

The first reading report creation processing is finished as described above.

Figure 8:
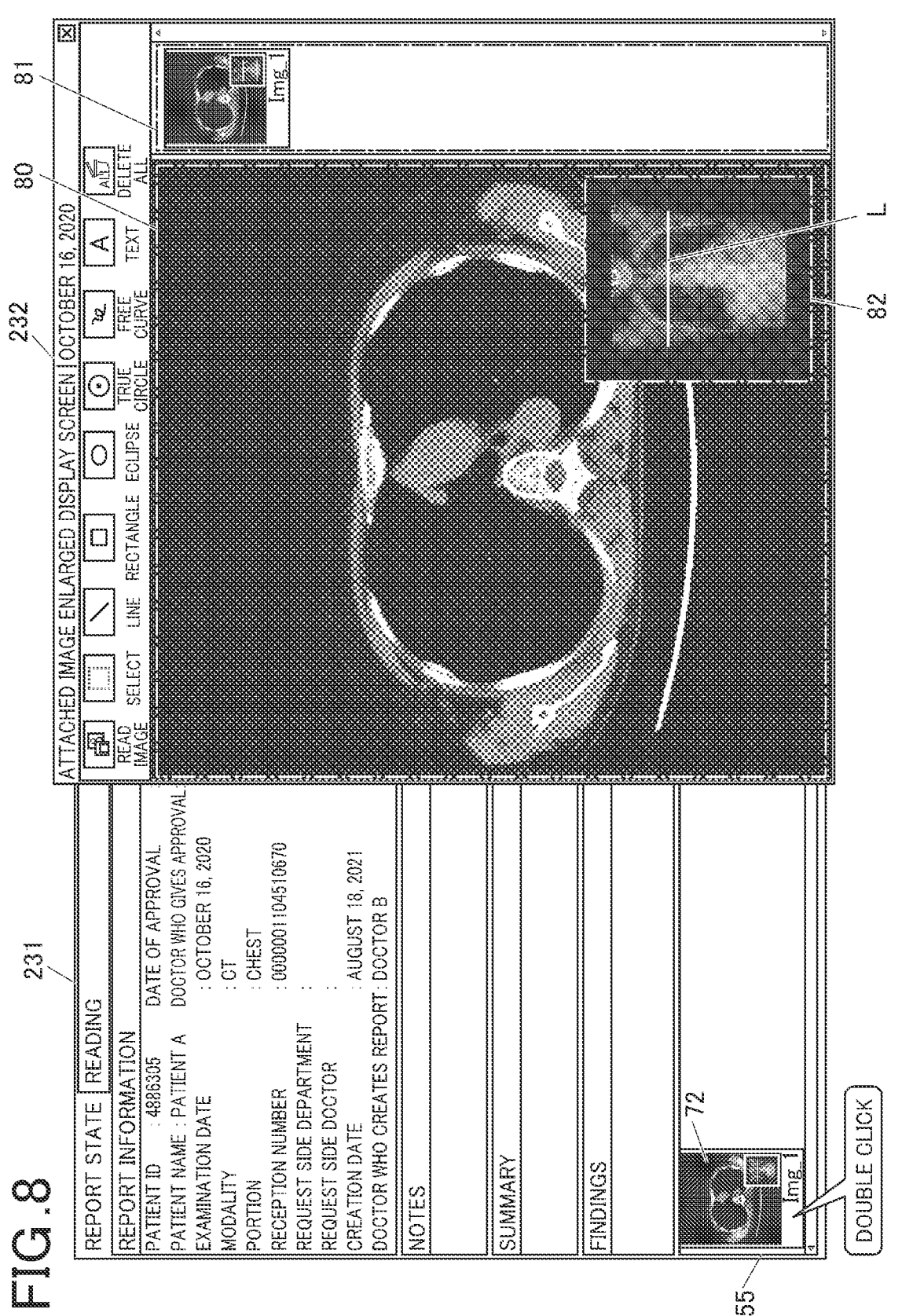
FIG. 8 is a view for explaining operation when an attached image enlarged display screen is displayed.

As illustrated in FIG. 8, if the user double clicks a synthesized image 72 through operation from the operation unit 22 in a state where the synthesized image 72 (image obtained by synthesizing the scout image in the predetermined region of the slice image) is displayed in the attached image display region 55 of the reading report creation screen 231 at the display 23 of the reading terminal 20, the controller 21 of the reading terminal 20 causes an attached image enlarged display screen 232 to be displayed at the display 23 of the reading terminal 20.

In the attached image enlarged display screen 232, a synthesized image is enlarged and displayed. The attached image enlarged display screen 232 includes a synthesized image display region 80 and an attached image display region 81. In the synthesized image display region 80, a synthesized image obtained by synthesizing the scout image in a lower right region 82 of the slice image is displayed. On the scout image in the synthesized image, a reference line L indicating a cross-section position of the slice image is added. In the attached image display region 81, an attached image displayed in the attached image display region 55 of the reading report creation screen 231 is displayed.

The reading report created through the first reading report creation processing is transmitted to the image management apparatus 10 from the reading terminal 20 and stored in the storage 13 of the image management apparatus 10 in a state where the synthesized image is attached. Further, the synthesized image itself obtained by synthesizing the scout image in the predetermined region of the slice image may be stored in the storage 13 of the image management apparatus 10 or the storage 25 of the reading terminal 20. Further, the synthesized image may be created every time the synthesized image is displayed instead of being stored in the storage 13 of the image management apparatus 10 or the storage 25 of the reading terminal 20.

As described above, according to the first embodiment, the synthesized image is created by synthesizing the scout image in the predetermined region of the slice image, so that the user can confirm the slice image and the scout image for specifying the cross-section position of the slice image only by viewing the created synthesized image. This makes it possible to recognize a correspondence relationship between the slice image and the scout image outside the image management apparatus 10.

Further, the synthesized image is created in a state where the reference line is added on the scout image, so that the cross-section position of the slice image on the scout image can be clearly specified.

Further, by displaying the created synthesized image at the display 23 of the reading terminal 20, it is possible to easily recognize a correspondence relationship between the slice image and the scout image.

Further, by transmitting the created synthesized image to an external apparatus (such as a medical image viewer), the synthesized image can be displayed at the external apparatus, so that it is possible to easily recognize a correspondence relationship between the slice image and the scout image.

Note that while in step S6 of the first reading report creation processing, the scout image is dragged and dropped on the slice image in the attached image display region 55 of the reading report while the Ctrl key is pressed, the scout image may be synthesized in the predetermined region of the slice image in the attached image display region 55 of the reading report only by the scout image being dragged and dropped on the slice image in the attached image display region 55 of the reading report without the Ctrl key being pressed. In other words, in a case where a predetermined user operation is performed (or in response to a predetermined user operation), the controller 21 of the reading terminal 20 creates a synthesized image by synthesizing the scout image in the predetermined region of the slice image. Here, the "predetermined user operation" corresponds to operation of dragging and dropping the scout image with respect to the slice image. Note that the "predetermined user operation" is not limited to the above-described operation.

Further, when the scout image is dragged and dropped with respect to the slice image, processing content may be changed in accordance with whether or not the Ctrl key is pressed. For example, in a case where the scout image is dragged and dropped on the slice image in the attached image display region 55 of the reading report without the Ctrl key being pressed, the scout image may be attached in a region adjacent to the slice image displayed in the attached image display region 55 of the reading report.

Further, in a case where the scout image is dragged and dropped on the slice image in the attached image display region 55 of the reading report while the Alt key is pressed instead of the Ctrl key, the scout image may be synthesized in the predetermined region of the slice image in the attached image display region 55 of the reading report.

Still further, on the reading report creation screen 231, by an "attach button" provided on the screen being pressed after the slice image that is desired to be attached to the reading report is selected, the slice image may be attached to the attached image display region 55 of the reading report. Further, by the "attach button" provided on the screen being pressed after the scout image that is desired to be attached to the reading report is selected in a state where the slice image is displayed in the attached image display region 55 of the reading report creation screen 231, the scout image may be synthesized in the predetermined region of the slice image in the attached image display region 55.

Second Embodiment

A second embodiment to which the present invention is applied will be described next.

An image management system in the second embodiment has a configuration similar to the configuration of the image management system 100 described in the first embodiment, and thus, FIG. 1 to FIG. 3 are employed, and illustration and description of the configuration will be omitted. Characteristic configuration and processing of the second embodiment will be described below.

The second embodiment is different from the first embodiment in an operation method when a slice image and a scout image are attached to a reading report.

The controller 21 of the reading terminal 20 creates a synthesized image by synthesizing the scout image in a predetermined region of the slice image in a case where the second user operation is performed in addition to the first user operation. Specifically, in a state where the slice image and the scout image are selected, operation of dragging and dropping the slice image with respect to a region in which the image is to be attached is used as the "first user operation", and pressing a predetermined key (such as the Ctrl key and the Alt key) is used as the "second user operation". Note that the "first user operation" and the "second user operation" are not limited to this example.

Operation in the image management system in the second embodiment will be described next.

Figure 9:
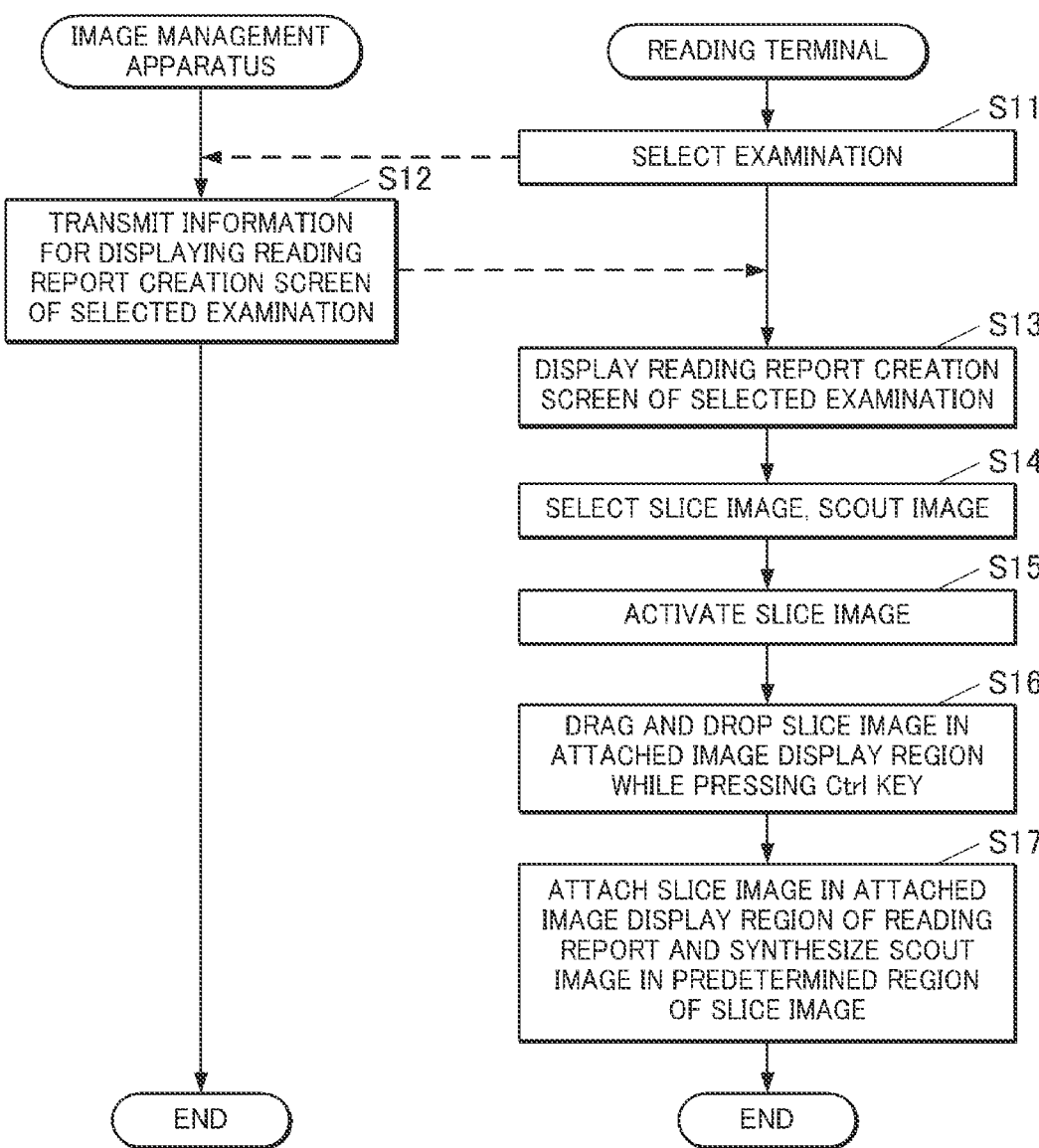
FIG. 9 is a ladder chart indicating second reading report creation processing in a second embodiment.

FIG. 9 is a ladder chart indicating second reading report creation processing to be executed at the image management apparatus 10 and the reading terminal 20.

The processing from step S11 to step S13 is similar to the processing from step S1 to step S3 in the first reading report creation processing (see FIG. 4) in the first embodiment, and thus, description will be omitted.

Then, on the reading report creation screen 231 (see FIG. 5, a configuration in the screen is similar to that in the first embodiment) to be displayed at the display 23 of the reading terminal 20, the user selects a slice image and a scout image through operation from the operation unit 22 (step S14). In a case where a plurality of images are selected in the image display regions 61 to 64 on the reading screen 60, it is only necessary to click images to be selected while pressing the Ctrl key.

Figure 10:
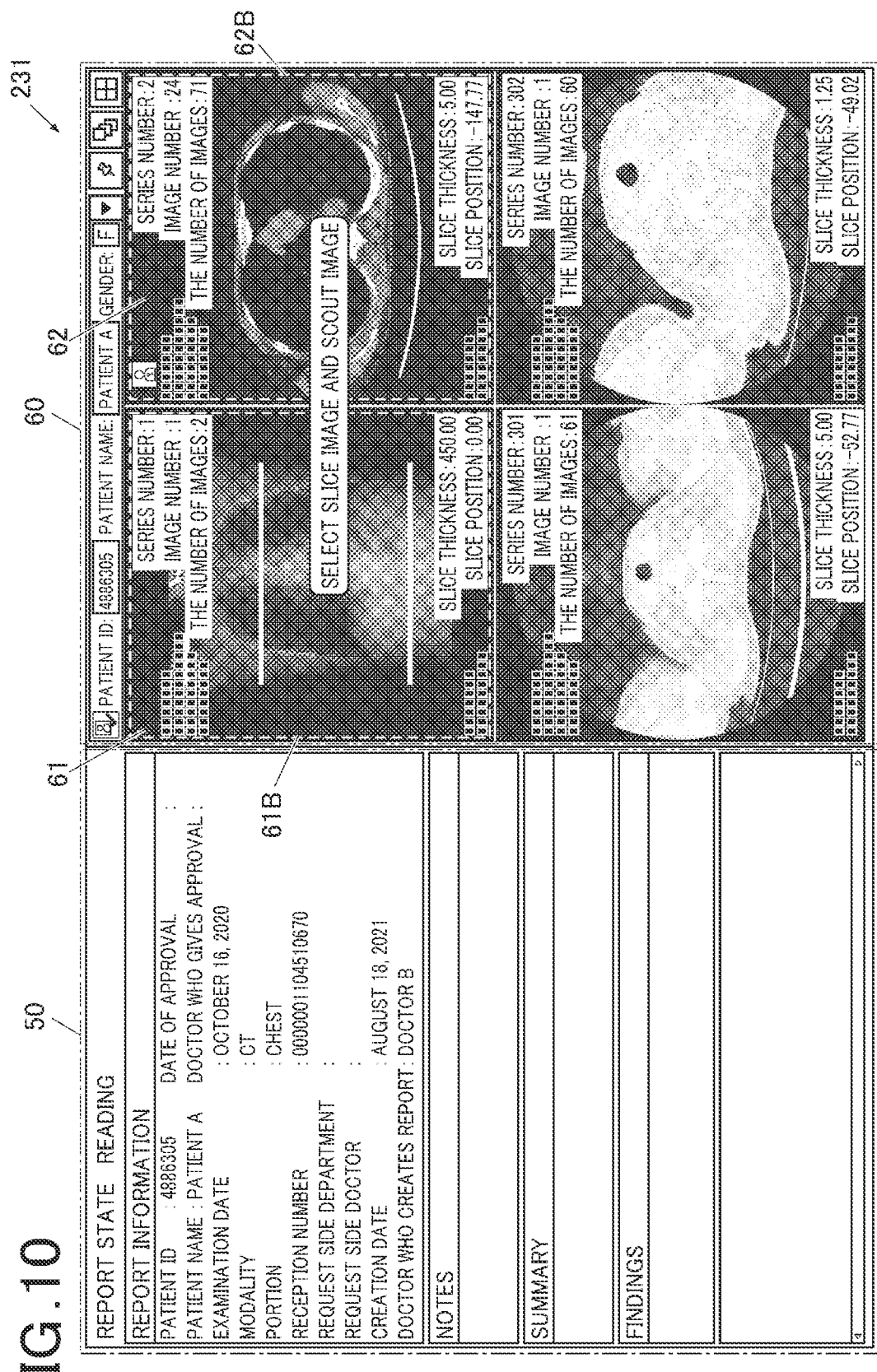
FIG. 10 is a view for explaining operation when a slice image and a scout image are selected on the reading report creation screen.

Specifically, on the reading report creation screen 231 illustrated in FIG. 10, if the user clicks the mouse on the slice image displayed in the image display region 62 while pressing the Ctrl key through operation from the operation unit 22, a selection frame 62B is displayed around the slice image. Then, if the user clicks the mouse on the slice image displayed in the image display region 61 while keeping the Ctrl key pressed, a selection frame 61B is displayed around the scout image. Here, the user releases the finger from the Ctrl key.

Then, the user activates the selected slice image through operation from the operation unit 22 on the reading report creation screen 231 displayed at the display 23 of the reading terminal 20 (step S15). Activation refers to setting of the image as an operation target.

Then, if the user drags and drops the slice image in the attached image display region 55 of the reading report while pressing the Ctrl key through operation from the operation unit 22 on the reading report creation screen 231 (step S16), the controller 21 of the reading terminal 20 attaches the slice image in the attached image display region 55 of the reading report and synthesizes the scout image in the predetermined region of the slice image (step S17). In other words, the controller 21 creates the synthesized image by synthesizing the scout image in the predetermined region of the slice image. Here, the controller 21 creates the synthesized image in a state where a reference line indicating a cross-section position of the slice image is added on the scout image.

Figure 11:
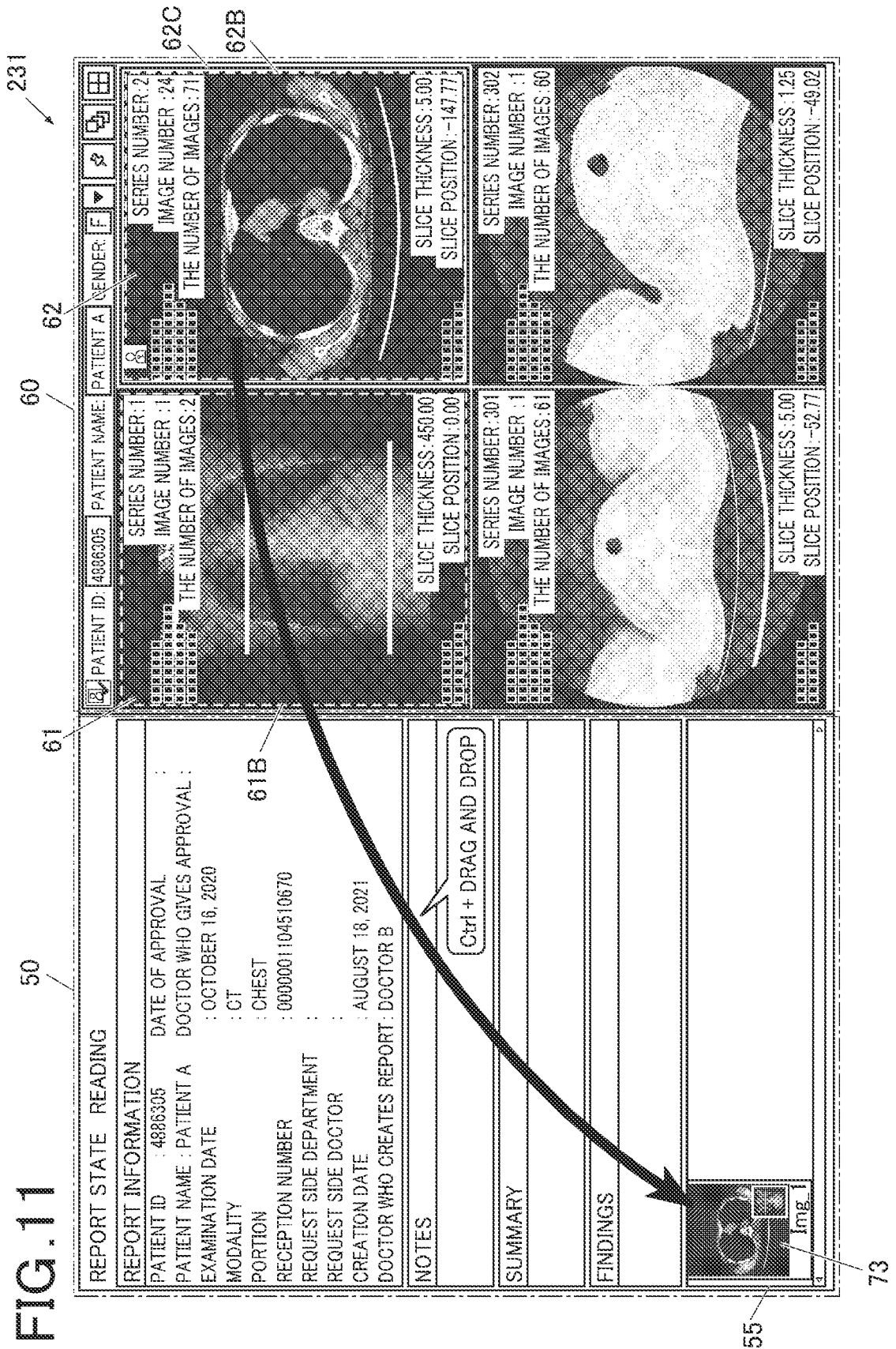
FIG. 11 is a view for explaining operation when a synthesized image obtained by synthesizing the scout image in a predetermined region of the slice image is attached on the reading report on the reading report creation screen.

Specifically, on the reading report creation screen 231 illustrated in FIG. 11, if the user presses the left button of the mouse on the slice image displayed in the image display region 62 while pressing the Ctrl key through operation from the operation unit 22, an operation target frame 62C is displayed around the slice image (activated). Then, if the user moves the mouse pointer from the slice image to the attached image display region 55 while keeping the left button of the mouse pressed through operation from the operation unit 22 and then releases the finger from the left button of the mouse (drags and drops), a synthesized image 73 is displayed in the attached image display region 55 of the reading report. Note that the user releases the finger that has pressed the Ctrl key after dragging and dropping the slice image. The synthesized image 73 is an image obtained by synthesizing the scout image in a lower right region of the slice image, and a reference line indicating the cross-section position of the slice image is added on the scout image.

The second reading report creation processing is finished as described above.

As described above, according to the second embodiment, the synthesized image is created by synthesizing the scout image in the predetermined region of the slice image, so that the user can confirm the slice image and the scout image for specifying the cross-section position of the slice image only by viewing the created synthesized image. This can make it possible to recognize a correspondence relationship between the slice image and the scout image outside the image management apparatus 10.

Further, the synthesized image is created in a state where the reference line is added on the slice image, so that the cross-section position of the slice image on the scout image can be clearly specified.

Further, by displaying the created synthesized image at the display 23 of the reading terminal 20, it is possible to easily recognize a correspondence relationship between the slice image and the scout image.

Further, by transmitting the created synthesized image to an external apparatus, the synthesized image can be displayed at the external apparatus, so that it is possible to easily recognize a correspondence relationship between the slice image and the scout image.

Note that while in step S16 in the second reading report creation processing, the slice image is dragged and dropped to the attached image display region 55 of the reading report while the Ctrl key is pressed, the synthesized image (image obtained by synthesizing the scout image in the predetermine region of the slice image) may be displayed in the attached image display region 55 of the reading report only by the slice image being dragged and dropped in the attached image display region 55 of the reading report without the Ctrl key being pressed. In other words, the controller 21 of the reading terminal 20 creates a synthesized image by synthesizing the scout image in the predetermined region of the slice image in a case where a predetermined user operation is performed. Here, the "predetermined user operation" corresponds to operation of dragging and dropping the slice image with respect to the attached image display region 55 in a state where the slice image and the scout image are selected. Note that the "predetermined user operation" is not limited to the above-described operation.

Further, when the slice image is dragged and dropped with respect to the attached image display region 55, processing content may be changed in accordance with whether or not the Ctrl key is pressed. For example, in a case where the slice image is dragged and dropped to the attached image display region 55 of the reading report in a state where the slice image and the scout image are selected without the Ctrl key being pressed, the slice image and the scout image may be attached side by side in the attached image display region 55 of the reading report.

Further, in a case where the slice image is dragged and dropped to the attached image display region 55 of the reading report while the Alt key is pressed instead of the Ctrl key in a state where the slice image and the scout image are selected, the synthesized image may be displayed in the attached image display region 55 of the reading report.

Further, on the reading report creation screen 231, by the "attach button" provided on the screen being pressed after the slice image and the scout image that are desired to be attached to the reading report are selected, the synthesized image may be attached to the attached image display region 55 of the reading report.

Third Embodiment

A third embodiment to which the present invention is applied will be described next.

An image management system in the third embodiment has a configuration similar to the configuration of the image management system 100 described in the first embodiment, and thus, FIG. 1 to FIG. 3 are employed, and illustration and description of the configuration will be omitted. Characteristic configuration and processing of the third embodiment will be described below.

The controller 11 of the image management apparatus 10 processes information stored in the image management apparatus 10 that stores a slice image and a scout image for specifying a cross-section position of the slice image.

The controller 11 (output means, a hardware processor) of the image management apparatus 10 outputs the slice image, the scout image, and association information that associates the slice image with the scout image to outside.

The association information is information for specifying the cross-section position of the slice image on the scout image. As the information for specifying the cross-section position of the slice image, for example, a combination of an imaging start portion, a slice thickness and an image number included in the supplementary information of the slice image is used.

Operation in the image management system in the third embodiment will be described next.

Figure 12:
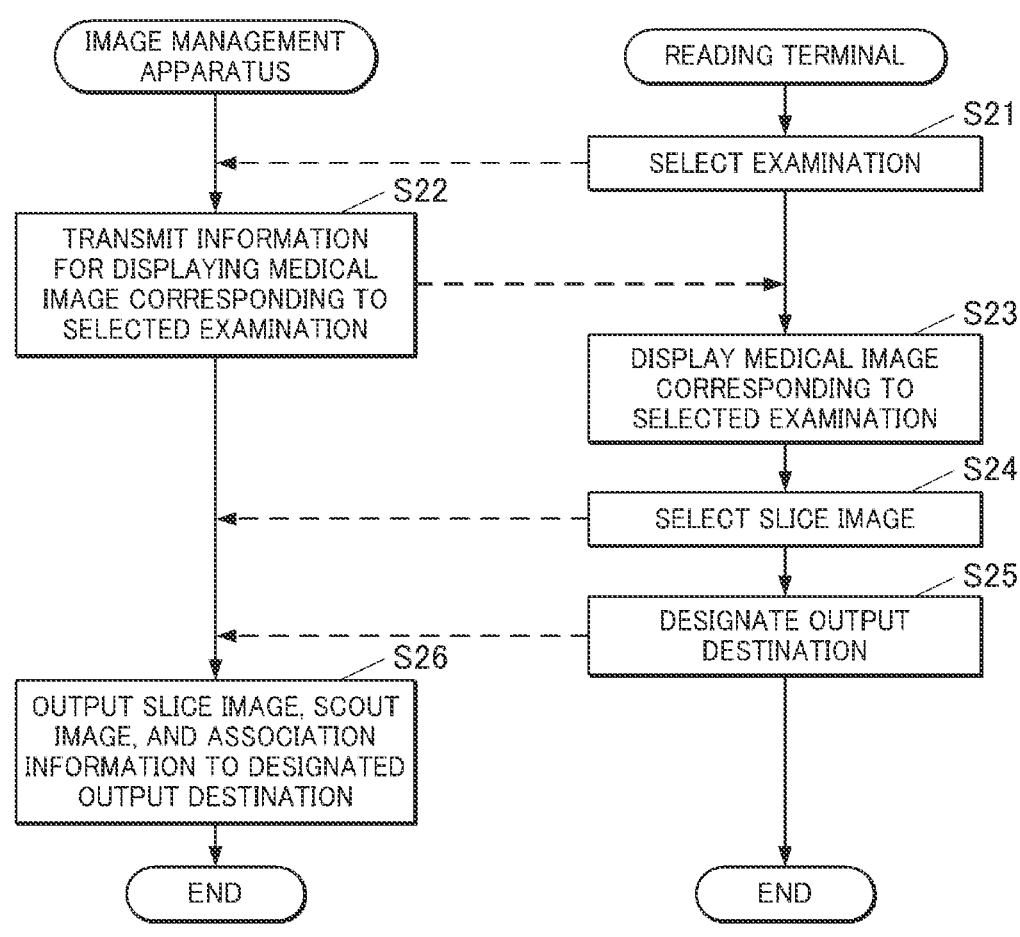
FIG. 12 is a ladder chart indicating association information creation processing in a third embodiment.

FIG. 12 is a ladder chart indicating association information creation processing to be executed at the image management apparatus 10 and the reading terminal 20.

The processing in step S21 is similar to the processing in step S1 in the first reading report creation processing (see FIG. 4) in the first embodiment, and thus, description will be omitted.

Then, the controller 11 of the image management apparatus 10 transmits information for displaying a medical image corresponding to the selected examination to the reading terminal 20 via the communicator 12 (step S22). Here, the selected examination is an examination such as CT and MRI, in which medical images including the slice image are generated.

Specifically, the controller 11 extracts a record including an "examination instance UID" corresponding to the selected examination from the image management table 132 stored in the storage 13 and acquires medical images relating to the selected examination from the image storage 133 on the basis of a "file path" included in the extracted record. Then, the controller 11 transmits each medical image to the reading terminal 20 via the communicator 12 along with supplementary information such as a "series number" and an "image type" included in the extracted record.

The controller 21 of the reading terminal 20 acquires information for displaying the medical images corresponding to the selected examination from the image management apparatus 10 via the communicator 24 and causes the medical images corresponding to the selected examination to be displayed at the display 23 (step S23).

Specifically, the controller 21 causes each medical image acquired from the image management apparatus 10 to be displayed at the display 23 for each series on the basis of the "series number" of each medical image.

Further, the controller 21 acquires whether the medical image is a slice image or a scout image from the "image type" of each medical image acquired from the image management apparatus 10. The controller 21 causes only a representative image in the same series to be initially displayed for the slice image and switches the representative image to a slice image of another image number in accordance with the user operation.

At the display 23 of the reading terminal 20, the medical images (the slice image, the scout image) corresponding to the selected examination are displayed.

At the reading terminal 20, the user performs operation from the operation unit 22 to select one slice image from the medical images displayed at the display 23 (step S24) and designates an output destination (step S25). The output destination may be an external apparatus or a storage medium that stores data. The controller 21 of the reading terminal 20 transmits information indicating the selected slice image and information indicating the designated output destination to the image management apparatus 10 via the communicator 24.

The controller 11 of the image management apparatus 10 receives the information indicating the selected slice image and the information indicating the designated output destination from the reading terminal 20 via the communicator 12. The controller 11 acquires an imaging start position, a slice thickness and an image number corresponding to the selected slice image from the image management table 132 and sets these kinds of information as the association information. Then, the controller 11 outputs the selected slice image, a scout image corresponding to the slice image (the scout image specified by the same examination instance UID as the selected slice image) and the association information to the designated output destination (step S26). For example, the controller 11 transmits the slice image, the scout image and the association information that are associated with each other, to an external apparatus designated as the output destination via the communicator 12. Further, the controller 11 causes the slice image, the scout image and the association information that are associated with each other, to be stored in a storage medium designated as the output destination.

The association information creation processing is finished as described above.

The external apparatus acquires the slice image, the scout image and the association information output from the image management apparatus 10. Specifically, the external apparatus acquires the slice image, the scout image and the association information by receiving the information transmitted from the image management apparatus 10 or reading the information stored in the storage medium.

The external apparatus calculates a distance from the imaging start position in a direction orthogonal to an image plane of the slice image on the basis of the slice thickness and the image number included in the association information and calculates a cross-section position of the slice image on the basis of the distance and the imaging start position included in the association information. Then, the external apparatus adds a reference line indicating the cross-section position of the slice image on the scout image when the slice image and the scout image are displayed.

As described above, according to the third embodiment, the slice image, the scout image and the association information that associates the slice image with the scout image are output to outside, so that the cross-section position of the slice image on the scout image can be specified on the basis of the association information at the output destination. This can make it possible to recognize a correspondence relationship between the slice image and the scout image outside the image management apparatus 10.

While in the third embodiment, the slice image, the scout image and the association information are output to outside for the slice image selected in step S24, a plurality of combinations of slice images, a scout image (common to all slice images) and association information may be output for each of the slice images in the same series captured in a predetermined examination.

Note that the above-described embodiments are examples of the non-transitory computer readable storage medium storing instructions, the image management apparatus, the reading terminal, and the image management system according to one or more embodiments of the present invention, and the present invention is not limited thereto. Detailed configurations and detailed operation of the respective apparatuses that constitute the system can be changed as appropriate within a range not deviating from the gist of the present invention.

For example, characteristic processing of the respective embodiments may be combined.

Further, the image management apparatus 10 and the reading terminal 20 (image display apparatus) may be integrally constituted. Specifically, the image management apparatus 10 may include an operation unit and a display and may cause a synthesized image, or the like, obtained by synthesizing a scout image in a predetermined region of a slice image to be displayed at the display of the image management apparatus 10 in accordance with operation from the operation unit of the image management apparatus 10.

Further, while in the first embodiment and the second embodiment, a scout image is synthesized in a lower right region of a slice image, the scout image may be synthesized in other regions in the slice image. However, the region may be a region that does not inhibit display of the slice image.

Further, while a case has been described in the first embodiment and the second embodiment where the synthesized image obtained by synthesizing the scout image in the predetermine region of the slice image is attached to the reading report, the output destination (attachment destination) of the synthesized image is not limited to this, and the synthesized image may be attached to an electronic health record, or the like, in which medical action performed on a patient and a diagnosis result are recorded.

Further, while in the first embodiment and the second embodiment, the controller 21 of the reading terminal 20 creates the synthesized image by synthesizing the scout image in the predetermined region of the slice image, the image management apparatus 10 side may create the synthesized image.

Specifically, the controller 11 (creation means, a hardware processor) of the image management apparatus 10 creates the synthesized image by synthesizing the scout image in the predetermined region of the slice image on the basis of the slice image selected at the operation unit 22 of the reading terminal 20 and the scout image corresponding to the slice image. Here, the controller 11 creates the synthesized image in a state where a reference line indicating a cross-section position of the slice image is added on the scout image. The controller 11 then outputs the created synthesized image (displays at the display 23 of the reading terminal 20, transmits to an external apparatus, and the like). Operation for creating the synthesized image may be similar to or different from the operation in the first embodiment and the second embodiment.

Further, while in the above-described embodiments, the slice image and the scout image generated in the same examination are associated with each other with the "examination instance UID" included in the supplementary information of the medical image, information for allowing the slice image and the scout image to be recognized as the images of the same examination is not limited to this.

Further, while in the above-described embodiments, distinction between the slice image and the scout image is recognized by the "image type" included in the supplementary information of the medical image, information for distinguishing between the slice image and the scout image is not limited to this.

A computer-readable medium that stores instructions for executing each kind of processing is not limited to the above-described example, and a portable recording medium can be applied. Further, as a medium that provides data of the instructions via a communication line, a carrier wave may be applied.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A non-transitory computer readable storage medium storing instructions causing a computer that processes information stored in an image management apparatus to execute:

in response to a user operation to drag and drop a scout image on a slice image while pressing a predetermined key, creating a synthesized image in which the scout image is synthesized at a predetermined position within the slice image, and displaying the synthesized image on a reading report, and in response to the user operation to drag and drop the scout image on the slice image while not pressing the predetermined key, displaying the slice image and the scout image side by side on the reading report, wherein the slice image and the scout image are stored in the image management apparatus, and the scout image specifies a cross-section position of the slice image.

2. The storage medium according to claim 1, wherein the creating includes creating the synthesized image in a state where a reference line indicating the cross-section position of the slice image is added on the scout image.

3. The storage medium according to claim 1, wherein the creating includes creating the synthesized image in response to a predetermined user operation.

4. The storage medium according to claim 1, wherein the creating includes creating the synthesized image in response to a second user operation performed in addition to a first user operation.

5. The storage medium according to claim 1, wherein the instructions further cause the computer to execute:
   outputting the synthesized image created in the creating.

6. An image management apparatus comprising:
a storage that stores a slice image and a scout image that specifies a cross-section position of the slice image; and
a hardware processor that:
   in response to a user operation to drag and drop the scout image on the slice image while pressing a predetermined key, creates a synthesized image in which the scout image is synthesized at a predetermined position within the slice image, and displaying the synthesized image on a reading report, and
   in response to the user operation to drag and drop the scout image on the slice image while not pressing the predetermined key, displaying the slice image and the scout image side by side on the reading report.

7. A reading terminal that processes information stored in an image management apparatus, the reading terminal comprising:
a hardware processor that:
   in response to a user operation to drag and drop a scout image on a slice image while pressing a predetermined key, creates a synthesized image in which the scout image is synthesized at a predetermined position within the slice image, and displaying the synthesized image on a reading report, and
   in response to the user operation to drag and drop the scout image on the slice image while not pressing the predetermined key, displaying the slice image and the scout image side by side on the reading report, wherein
the slice image and the scout image are stored in the image management apparatus, and
the scout image specifies a cross-section position of the slice image.

8. An image management system comprising:
an image management apparatus that stores a slice image and a scout image that specifies a cross-section position of the slice image; and a hardware processor that:

in response to a user operation to drag and drop the scout image on the slice image while pressing a predetermined key, creates a synthesized image in which the scout image is synthesized at a predetermined position within the slice image, and displaying the synthesized image on a reading report, and in response to the user operation to drag and drop the scout image on the slice image while not pressing the predetermined key, displaying the slice image and the scout image side by side on the reading report.

\* \* \* \* \*